United States Patent [19]
Lansky

[11] Patent Number: 5,891,440
[45] Date of Patent: Apr. 6, 1999

[54] PHYTOESTROGEN SUPPLEMENT PREPARED FROM POMEGRANATE SEEDS AND A HERBAL MIXTURE OR COCONUT MILK

[76] Inventor: Ephraim Philip Lansky, P.O. Box 6070, Haifa, 31060, Israel

[21] Appl. No.: 777,895

[22] Filed: Dec. 31, 1996

[51] Int. Cl.⁶ .................................................... A61K 35/78
[52] U.S. Cl. ........................................ 424/195.1; 514/874
[58] Field of Search ......................... 424/195.1; 514/874

[56] References Cited

U.S. PATENT DOCUMENTS 5,424,331  6/1995  Shlyankevich ........................... 514/456

FOREIGN PATENT DOCUMENTS 1080492  1/1994  China .
1251851  8/1986  U.S.S.R. .

OTHER PUBLICATIONS

Markh et al., Izv. Vyssh. Uchebn. Zaved., Pishch. Tekhnol., 4:120–123, English translation of abstract, 1984.
Trease and Evans' Pharmacognosy, Bailliere Tindall, London, GB, p. 391, 1989.
Singh et al., Indian Food Packer, 47:9–15, 1993.
Moneam et al., J. Chromatogr., 438:438–442, 1988.
El–Nemr et al., Die Nahrung, 34:601–606, 1990.
Mowrey, The Scientific Validation of Herbal Medicine, Keats Publishing, Inc., CT, p. 109, 1986.
Reid, A Handbook of Chinese Healing Herbs, Shambhala Publications, Inc., MA, pp. 57, 58, and 173–175, 1995.
Quisumbing, Medicinal Plants of the Philippines, Manila Bureau of Printing, pp. 127–132, 1951.
Knight et al., Maturitas, 22:167–175, 1995.
Creidi et al., Maturitas, 19:211–223, 1994.
Remington's Pharmaceutical Sciences, 16th ed., Mack Publishing Co., PA, pp. 1248–1252, 1259, and 1260, 1980.

*Primary Examiner*—David M. Naff
*Assistant Examiner*—Janet M. Kerr
*Attorney, Agent, or Firm*—Mark M. Friedman

[57] ABSTRACT

A phytoestrogen oral supplement and ointment, and methods of preparing the supplement and ointment, are described. The oral phytoestrogen supplement is prepared by extracting pomegranate seeds with an aqueous solvent, and admixing the pomegranate seed extract with an herbal extract containing shizandra berries, Chinese asparagus root, and optionally Chinese licorice root and Chinese angelica root. The phytoestrogen ointment is prepared by pressing pomegranate seeds to obtain a pomegranate seed oil, and mixing the pomegranate seed oil with coconut milk to form the ointment. The phytoestrogen ointment can also contain an ethanolic extract of Chinese asparagus root and schizandra berries.

22 Claims, No Drawings

PHYTOESTROGEN SUPPLEMENT PREPARED FROM POMEGRANATE SEEDS AND A HERBAL MIXTURE OR COCONUT MILK

FIELD AND BACKGROUND OF THE INVENTION

The present invention relates to phytoestrogen supplements and, more particularly, to phytoestrogen supplements derived from botanical sources which can be administered in a variety of ways.

Steroidal estrogens are typically derived from animal sources and are used to treat conditions such as menopause. Menopause occurs as ovarian function gradually declines, leading to the cessation of ovulation, menstruation and finally secretion of estrogen by the ovaries. The decline and cessation of estrogen secretion leads to a number of symptoms, including hot flashes, mood disturbances such as depression, atheromatous disease and osteoporosis.

Although animal-derived steroidal estrogens, such as estradiol, estratriol and estrone, can be successfully used to treat these symptoms, many women are reluctant to take these substances, and many medical professionals are equally reluctant to prescribe them. These estrogens have been linked to an increase in cancer in women to whom they were administered. Thus, it would be advantageous to find a substance or group of substances which mimic the desirable effects of estrogens, namely the cessation of symptoms associated with menopause, yet which are not carcinogenic.

Phytoestrogens are non-steroidal compounds found in a variety of plants, which exert estrogenic effects in animals. Phytoestrogens from botanical materials may reduce the frequency of hot flashes in Japanese women. Such phytoestrogens were shown to be excreted at a high level in the urine of these women, and are associated with a high level of intake of soy products which contain phytoestrogens [Adlercreutz, H., Hamalainen, E., Gorbach, S. and B. Goldin, *The Lancet*, 1992, 339:1233]. Estrogenic effects were shown in postmenopausal women after dietary supplementation with soy flour and linseed, which contain phytoestrogens [Wilcox, G., Wahlqvist, M. L., Burger, H. G. and G. Medley, *British Medical Journal*, 1990, 301:905–6].

Such phytoestrogens are known to be present in pomegranate seeds. The level of phytoestrogens was measured by preparing an acetone extract of the pomegranate seeds and then subjecting this extract to HPLC (High Performance Liquid Chromatography) [Moneam, N. M. A., El Sharaky A. S. and M. M. Radreldin, *Journal of Chromatography*, 1988, 438:438–442]. Both non-steroidal phytoestrogens and steroidal estrogen were found in the extract.

The estrogenic activity of another preparation of pomegranate seeds has also been described in ovariectomized mice and immature rabbits [A. Sharaf and S. A. R. Nigm, *Journal of Endocrinology*, 1964, 29:91–92]. This preparation was made by extracting the pomegranate seeds with ether and showed clear estrogenic activity in both the mice and the rabbits, specifically measured by cornification of the vaginal cells and an increase in uterine weight.

The presence of sex hormone-like substances in milk from immature coconuts has also been demonstrated [B. Punghmatharith, *Warasan Songkhla Nakkharin*, 1988, 10:221–226]. Furthermore, these substances were shown to have estrogenic activity in rats, altering the uterine growth in these animals.

As noted above, a number of botanical materials have been shown to contain phytoestrogens, such as soybeans from *Soja max*. Other sources of phytoestrogens include *Glycyrrhiza glabrata* or liquorice, *Medicago sativa* or alfalfa and *Malus sylvestris* or apple [K. R. Price and G. R. Fenwick, *Food Additives and Contaminants*, 1985, 2:73–106].

Although such phytoestrogens have only recently come to the attention of Western medicine, the use of plants to treat female patients for conditions related to the reproductive system has been known in Chinese medicine for hundreds of years. For example, Chinese angelica root (*Angelica sinensis*), Chinese licorice root (*Glycyrrhizae uralensis*), Chinese asparagus root (*Asparagus lucidus*) and schizandra berries (*Schizandra chinensis*) have all been used in Chinese herbal medicine to treat female patients, specifically for complaints concerning the reproductive system [*Chinese Tonic Herbs*, by R. Teeguarden, Japan Publications, New York, 1985]. Typically, preparations containing these botanical materials were given orally, and were considered to be highly effective.

Other examples of botanical preparations include skin creams. A cream for oily skin has been prepared which includes a carbonic acid extraction of rinds and seeds of pomegranates, as described in USSR Patent No. 1,602,533. However, such an extract has the disadvantage of being prepared with carbonic acid, rather than with a less toxic solvent. Furthermore, no suggestion was made that such an extract could also be used as an oral phytoestrogen supplement, rather than simply as a topically applied skin cream. Certainly, if such an extract were to be used orally, a less toxic solvent would be needed.

There is thus a widely recognized need for, and it would be highly advantageous to have, an oral phytoestrogen supplement prepared from pomegranate material, such as pomegranate seeds, as well as a skin cream prepared from such material. Furthermore, it would be advantageous to include other botanical sources of phytoestrogens for increased effectiveness of the oral supplement and skin cream. Finally, it would be advantageous to use these sources of phytoestrogens in a vaginal cream.

SUMMARY OF THE INVENTION

According to the present invention there is provided an oral phytoestrogen supplement, as well as a method of preparing the oral phytoestrogen supplement, including the step of contacting pomegranate material with an appropriate solvent to form a pomegranate extract, the extract being suitable for oral administration. Preferably, the solvent includes water and ethanol. Also preferably, the pomegranate material includes crushed pomegranate seeds.

According to preferred embodiments of the present invention, the method further includes the steps of: (b) contacting a herbal mixture with water to form an aqueous extract, the herbal mixture including schizandra berries and Chinese asparagus root; and (c) mixing the aqueous extract with the pomegranate extract to form a mixture.

According to further preferred embodiments of the present invention, the method further includes the steps of: (d) filtering the mixture to remove solid material to form a filtered mixture; (e) heating the solid material until the solid material is substantially carbonized, forming carbonized solid material; (f) extracting the carbonized solid material with water to form a second aqueous extract; and (g) mixing the aqueous extract with the filtered mixture to form a second mixture. Preferably, the herbal mixture further includes Chinese licorice root and Chinese angelica root. Also preferably, the ratio of the Chinese licorice root to the Chinese asparagus root to the Chinese angelica root to the schizandra berries is about 2:2:1:2. Most preferably, a weight of the Chinese licorice root is about 300 g, a weight of the Chinese asparagus root is about 300 g, a weight of the Chinese angelica root is about 150 g and a weight of the schizandra berries is about 300 g.

According to another embodiment, there is provided an ointment and a method of preparing the ointment, including the steps of (a) preparing pomegranate oil by pressing pomegranate seeds; and (b) mixing the pomegranate oil with coconut milk to form a mixture.

According to preferred embodiments of the present invention, the method further includes the steps of: (c) preparing an extract of Chinese asparagus root and schizandra berries by contacting the Chinese asparagus root and the schizandra berries with ethanol; and (d) adding the extract to the mixture. Most preferably, the method further includes the step of: (e) adding a pharmaceutically appropriate carrier to the mixture. Preferably, the pharmaceutically appropriate carrier includes beeswax and cocoa butter, or alternatively and preferably, hydrophilic lanolin. Also preferably, a ratio of the pomegranate oil to the coconut milk to the extract of the Chinese asparagus root to the extract of the schizandra berries is about 40:20:3:3. Most preferably, a weight of the pomegranate oil is about 40 g, a weight of the coconut milk is about 20 g, a weight of the extract of the Chinese asparagus root is about 3 g and a weight of the extract of the schizandra berries is about 3 g.

According to yet another embodiment, there is provided a method of preparing a phytoestrogen supplement, comprising the step of contacting pomegranate material with a solvent selected from the group consisting of water and ethanol to form a pomegranate extract. Preferably, the pomegranate material includes crushed pomegranate seeds. More preferably, the method further includes the steps of: (b) contacting a herbal mixture with water to form an aqueous extract, the herbal mixture including schizandra berries and Chinese asparagus root; and (c) mixing the aqueous extract with the pomegranate extract to form a mixture. Most preferably, the method further includes the steps of: (d) filtering the mixture to remove solid material and to form a filtered mixture; (e) heating the solid material until the solid material is substantially carbonized, forming carbonized solid material; (f) extracting the carbonized solid material with water to form a second aqueous extract; and (g) mixing the aqueous extract with the filtered mixture to form a second mixture.

DESCRIPTION OF THE PREFERRED EMBODIMENTS

The present invention is of phytoestrogen supplements which can be administered in a variety of ways, including topically and orally. Specifically, the present invention can be used to relieve symptoms in menopausal women, including hot flashes and mood disturbances when given orally, and vaginal dryness and lack of skin tone when administered topically.

The invention is illustrated by the following examples, which describe the preparation and use of phytoestrogen supplements to relieve symptoms in menopausal or postmenopausal women.

EXAMPLE 1

Method of Preparation of Phytoestrogen Supplements

The following botanical materials were used to prepare various embodiments of the phytoestrogen supplement: pomegranate material, preferably pomegranate seeds (*Punica granatum*), schizandra berries (*Schizandra chinensis*), Chinese licorice root (*Glycyrrhizae uralensis*), Chinese asparagus root (*Asparagus lucidus*) and Chinese angelica root (*Angelica sinensis*). The pomegranate seeds were preferably fresh with intact juice sacs. The schizandra berries were preferably dried. The three roots, Chinese licorice root, Chinese asparagus root and Chinese angelica root, were all preferably dried and cut.

The basis of the phytoestrogen supplement of Example 1 was a preparation of the pomegranate material, preferably pomegranate seeds, which were contacted with an appropriate solvent as described below, preferably including water and ethanol, to form an extract. If the supplement was intended as an oral phytoestrogen supplement, the extract was suitable for oral administration. For example, to make such an extract suitable for oral administration, the solvents were substantially non-toxic to the subject, so that there should not be an untoward level of adverse side effects, such as toxicity, irritation, allergy or hypersensitivity responses. The level of any such side effects should be commensurate with acceptable risk/benefit ratios. Examples of such substantially non-toxic solvents include water and ethanol. Otherwise, the extract is preferably prepared by contacting a preparation of the omegranate material, preferably pomegranate seeds, with a solvent selected from the group consisting of water and ethanol.

Preferably, the supplement also included a herbal mixture, including schizandra berries and Chinese asparagus root, and most preferably including Chinese licorice root and Chinese angelica root.

The method of preparation was as follows. First, about ten liters of whole pomegranate seeds were slowly added to a standard kitchen blender, and were homogenized for about twenty seconds at a low speed, so that the juice was released and the seeds were coarsely crushed. Hereinafter, the term "crushed" also includes chopped, pressed or squeezed.

Preferably, an aqueous extract was prepared next by placing about 300 g of schizandra berries, about 300 g each of Chinese licorice root and Chinese asparagus root, and about 150 g of Chinese angelica root, in a large pot with six liters of distilled water. The ratio of these ingredients was thus about 2:2:1:2 Chinese licorice root to Chinese asparagus root to Chinese angelica root to schizandra berries. Preferably, the contents were brought to a boil, covered and allowed to simmer for about three hours over a low flame. The mixture was then allowed to cool at room temperature.

The pomegranate seeds and juice were then placed in a sterilized bottle, preferably about five gallons in volume. The aqueous extract was also preferably added to the bottle, forming a mixture. Preferably, about 5 g of wine yeast, most preferably Lalvin™ EC-1118, Lallemand Inc., Montreal, Canada, was added to the bottle and a sterile surgical glove affixed to the mouth of the bottle with a rubber band. The bottle was preferably then put in a warm place so that fermentation occurred, which was allowed to proceed to completion, taking approximately ten days. The glove acted as an escape valve to prevent the build-up of gases.

After fermentation, the glove was removed and the contents of the bottle were preferably topped off with an ordinary dry red wine, most preferably Carmel Hilonim™ 1995, Carmel Winery, Israel. About two liters of this wine was added to the bottle. The bottle was then preferably sealed and placed in a cool, dark place for about three months.

After three months, the liquid contents of the bottle, which was the mixture of the pomegranate extract and the aqueous herbal extract, were preferably removed and strained through cheesecloth, leaving solid material in the bottle and forming a filtered extract. The water and alcohol were preferably gradually evaporated by placing the liquid in an uncovered pot over a very low flame, with an asbestos pad between the pot and the flame. After approximately 72 hours, the volume of liquid was reduced to about 10% of its original volume, resulting in a concentrated liquid. This heating process was performed carefully so that the liquid is not overheated and burned during this evaporation.

The concentrated liquid was preferably combined with an equal volume of unrefined bee honey and gently heated for a few minutes. This honey mixture was then placed in a brown glass bottle and set aside.

The solid material from the five-gallon bottle was then preferably placed in another glass bottle and covered with food grade alcohol, so that a second alcohol extract was obtained by contacting the solid material with ethanol. This bottle was then shaken briskly for several minutes twice each day for about three days. Next, the alcohol was preferably decanted and gradually evaporated, leaving a second solid material. Preferably, the evaporation is performed using a vacuum distillation apparatus, although for this Example the evaporation was performed by heating over a low flame. After evaporation, a syrup was obtained, which was added to the honey mixture in the brown glass bottle.

The second solid material was preferably heated at a high temperature until it burned, for example by placing the solid material in a kitchen oven with a high flame. The resultant black powder was then heated at a high temperature for about 72 hours until the powder was nearly white. Hereinafter, the term "carbonized solid material" includes either the black powder or the white powder, or a mixture thereof.

The carbonized solid material was then preferably added to at least ten times its volume of distilled water and heated almost to boiling for one hour while the mixture was continuously stirred, so that an aqueous extract was obtained by contacting the carbonized solid material with water. The aqueous extract was then preferably filtered through filter paper, and the remaining solid material discarded. This aqueous extract was preferably gradually heated over a low flame, until nearly all of the liquid had evaporated, leaving a concentrated solution of calcined salts.

This concentrated solution of calcined salts was then preferably added to the honey mixture in the brown glass bottle. This final mixture was then preferably gently heated and stirred to form the phytoestrogen supplement.

Alternatively and preferably, the phytoestrogen supplement can be mixed with pomegranate oil prepared according to the following method. First, pomegranate seeds were dried to remove excess moisture. The oil was then extracted from the seeds by pressing the seeds in a hydraulic oil press at room temperature. This oil is then mixed with the phytoestrogen supplement to form a combination of pomegranate oil and phytoestrogen supplement, of which up to about 50% (volume/volume) can be pomegranate oil. This combination is preferably placed in gelcaps as a pharmaceutical preparation, for ease of oral administration.

EXAMPLE 2

Methods of Preparation of Topical Phytoestrogen Supplements

The following botanical materials were used to prepare various embodiments of the topical phytoestrogen supplements: pomegranate material, preferably pomegranate seeds (*Punica granatum*), coconut milk (*Cocus nucifera*), schizandra berries (*Schizandra chinensis*) and Chinese asparagus root (*Asparagus lucidus*). The pomegranate seeds were preferably dried. The schizandra berries were also preferably dried. The Chinese asparagus root was preferably dried and cut. Preferably, the coconut milk was taken from immature coconuts. Most preferably, the coconut milk is combined with the coconut pulp, rapidly frozen at −40° C., dried under vacuum at pressures in a range from about 0.01 to about 1 mbar and then ground into a fine powder. Hereinafter, the term "coconut milk" includes either the liquid milk itself, or the fine powder prepared as described above.

The basis of the phytoestrogen supplements of Example 2 was a mixture of a preparation of the pomegranate material, preferably pomegranate seeds, which were pressed as described below to produce pomegranate oil, and of the coconut milk. Hereinafter, the term "pressed" also includes squeezed and crushed. Preferably, the supplements also included schizandra berries and Chinese asparagus root.

The method of preparation was as follows. First, pomegranate seeds were dried to remove excess moisture. The oil was extracted from the seeds by pressing the seeds in a hydraulic oil press at room temperature.

Preferably, extracts of Chinese asparagus root and schizandra berries were prepared by contacting these materials with food grade ethanol and using exhaustive Sohxtlett extraction. The alcohol was then preferably gradually removed, preferably by vacuum distillation, to form a solid. Alternatively, the extracts were prepared by placing about 500 g of each of these materials in about 4 liters of food grade alcohol contained in a glass vessel, closing the vessel and allowing it to rest in a cool, dark place for four months. In this case, the alcohol was removed by slow evaporation over a low flame with an asbestos pad for about 12 hours.

Preferably, about 15 g of bleached beeswax and about 15 g of cocoa butter were then melted in a warm water bath of about 80° C. These two substances do not contain phytoestrogens, but are added for ease of topical administration, and can form at least a portion of a pharmaceutically appropriate carrier.

About 40 g of pomegranate oil was added to these melted fats and continuously stirred. Next, about 20 g of coconut milk from immature coconuts was added to this mixture. Preferably, this milk was a commercially available canned coconut milk, Chaokoh™, Thep Padung Porn Coconut Co., Bangkok, Thailand. More preferably, the volume of the milk was reduced by about 80% by evaporation over a low flame with an asbestos pad. Most preferably, fresh immature coconut milk is freeze dried and the resulting powder is used.

Preferably, about 3 g of asparagus root extract and of schizandra berry extract were then added to the mixture to form a second mixture. The final ratio of the ingredients in the second mixture was thus about 40:20:3:3 pomegranate oil to coconut milk to extract of Chinese asparagus root to extract of schizandra berries. Preferably, a number of compounds was added to the second mixture for preservation of the supplement and for ease of topical administration: about 1 g of citric acid, about 1 g of boric acid and about 0.5 g each of methylparaben and of propylparaben. The resultant composition was preferably stirred continuously in the warm water bath for about 20 minutes, and then poured into containers and allowed to cool, forming the finished product for face cream and general skin care, hereinafter referred to as "skin cream".

To prepare an ointment for vaginal application, about 80 g of the cooled mixture was added to about 20 g of hydrophilic lanolin, such as Eucerin™, Beirsdorf Company, Hamburg, Germany, which was added for ease of topical administration and can form at least a portion of an appropriate pharmaceutical carrier. The resultant mixture was then preferably stirred continuously in a warm water bath until uniform and then poured into containers to cool. This product is hereinafter referred to as "vaginal ointment". Hereinafter, the term "ointment" includes the skin cream and vaginal ointment of the present invention.

EXAMPLE 3

Alternative Methods of Preparation of Skin Cream

Skin cream can also be prepared according to one of three alternative methods, using some or all of the botanical materials of Examples 1 and 2.

Alternative Method 1: First, the skin cream of Example 2 was prepared. Next, pomegranate rind extract was added to this skin cream, so that the fmal concentration of pomegranate rind extract in the skin cream was in the range of about 1% to about 10%, preferably about 3%. Preferably, this pomegranate rind extract was prepared by contacting pomegranate rinds with a suitable solvent, most preferably water.

The pomegranate rind extract was prepared as follows. First, rinds and 5 some seeds from the pomegranate fruit were placed in a pressure cooker, filling the cooker to about two-thirds of its full capacity. The contents of the pressure cooker were then covered with water and cooked for about 15 minutes under pressure. The resultant extract was then removed and heated until about 90% of the water was evaporated, to form a concentrated extract. Preferably, this extract is further concentrated by gentle heating for about 24 to about 48 hours to form a further concentrated extract. The further concentrated extract is then preferably mixed with an equal volume of bee honey.

Alternative Method 2: The following substitution can be made in the skin cream of Example 2. A pomegranate extract can be substituted for a portion of the pomegranate seed oil used in Example 2. This pomegranate extract is prepared by contacting pomegranate seeds and juice with an appropriate solvent, preferably ethanol.

This extract can be prepared by modifying the method of Example 1 to eliminate the addition of botanical material other than the pomegranate seeds and juice. First, about ten liters of whole pomegranate seeds were slowly added to a standard kitchen blender, and were homogenized for about twenty seconds at a low speed, so that the juice was released and the seeds were coarsely crushed. Hereinafter, the term "crushed" also includes chopped, pressed or squeezed.

The pomegranate seeds and juice were then placed in a sterilized bottle, preferably about five gallons in volume. Preferably, about 5 g of wine yeast, most preferably Lalvin™ EC-1118, Lallemand Inc., Montreal, Canada, was added to the bottle and a sterile surgical glove affixed to the mouth of the bottle with a rubber band. The bottle was preferably then put in a warm place so that fermentation occurred, which was allowed to proceed to completion, taking approximately ten days. The glove acted as an escape valve to prevent the build-up of gases.

After fermentation, the glove was removed and the contents of the bottle were preferably topped off with an ordinary dry red wine, most preferably Carmel Hilonim™ 1995, Carmel Winery, Israel. About two liters of this wine was added to the bottle. The bottle was then preferably sealed and placed in a cool, dark place for about three months.

After three months, the liquid contents of the bottle, which was the pomegranate extract, were preferably removed and strained through cheesecloth, leaving solid material in the bottle and forming a filtered extract. The water and alcohol were preferably gradually evaporated by placing the liquid in an uncovered pot over a very low flame, with an asbestos pad between the pot and the flame. After approximately 72 hours, the volume of liquid was reduced to about 10% of its original volume, resulting in a concentrated liquid. This heating process was performed carefully so that the liquid is not overheated and burned during this evaporation.

The concentrated liquid was preferably combined with an equal volume of unrefined bee honey and gently heated for a few minutes. This honey mixture was then placed in a brown glass bottle and set aside.

Alternative Method 3: A skin cream is prepared according to Example 2 above, but without the extracts of schizandra and Chinese asparagus. A phytoestrogen supplement is prepared according to Example 1 and is then added to the skin cream as about 6% of the total weight.

EXAMPLE 4

Methods of Administration of Phytoestrogen Supplements

The phytoestrogen supplement prepared according to the methods in Examples 1 and 2 can be administered to a patient in a number of ways, which are well known in the art. For example, administration may be done topically (including ophtalmically, vaginally, rectally, intranasally), orally, by inhalation, or parenterally, for example by intravenous drip or intraperitoneal, subcutaneous, or intramuscular injection.

Preferably, the phytoestrogen supplement prepared according to Example 1 is administered orally, and the phytoestrogen supplement prepared according to Example 2 is administered topically. Most preferably, the skin cream prepared according to Example 2 is administered to the skin of the patient, including but not limited to, the skin of the hands and face, and the vaginal ointment prepared according to Example 2 is administered to the vagina of the patient.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the patient to the phytoestrogen supplement. Persons of ordinary skill in the art can easily determine optimum dosages, dosing methodologies and repetition rates.

EXAMPLE 5

Case Histories of Treatment with Oral Phytoestrogen Supplements

Each of the following patients was treated with the phytoestrogen supplement prepared according to the most preferred embodiments of Example 1.

Case History 1: A fifty-two year old female reported a chief complaint of hot flashes which she felt over her entire body and which left her drenched in sweat. Each episode of hot flashes lasted about two minutes and recurred as often as ten times per day. These hot flashes had started about two months previously. Prior to the onset of these symptoms, her menses had been irregular and infrequent for about two years, and had ceased entirely over the previous two months. The patient was given 2 ml of the oral phytoestrogen supplement, prepared according to Example 1 above, to be taken three times a day. Within 24 hours, the patient reported that the hot flashes had almost ceased entirely. The patient continued taking the supplement daily for two weeks. During this period, a few hot flashes did occur, but these were of markedly less intensity. After several weeks, the symptoms did return, but were considerably more mild and less frequent than before treatment.

Case History 2: A fifty-four year old female complained of hot flashes since the cessation of her menses two years previously. Recently, the symptoms had increased both in intensity and frequency, and were occurring up to twenty times a day. After treatment three times a day for a two week period with 0.5 cc of the oral phytoestrogen supplement, prepared according to Example 1 above, the patient reported that the hot flashes had decreased in frequency to only about 3–4 times a day, were of shorter duration and considerably lower intensity. This improvement seemed to be permanent, even after the patient stopped taking the oral phytoestrogen supplement after about two months of treatment.

Case History 3: A forty-eight year old female reported feelings of depression and lack of interest in her usual activities after the cessation of her menses, two years previously. Also, she had difficulty controlling food cravings for chocolate, and would eat large amounts of chocolate at a single sitting. After treatment once a day with 0.5 cc of the oral phytoestrogen extract, prepared as in Example 1 above, she reported a significant amelioration of her depression and a concomitant decrease in her cravings for chocolate. The effect was noticeable after two weeks of treatment, and was also noticeable even six months after treatment, so the effect appeared to be permanent.

EXAMPLE 6

Case Histories of Treatment with Topical Phytoestrogen Supplements

Each of the following patients was treated with the phytoestrogen supplement prepared according to the most preferred embodiments of Example 2, except that evaporated, liquid coconut milk was used instead of the fine powder.

Case History 1: A forty-five year old female complained of wrinkled facial skin. After two weeks of applying the skin cream prepared according to the method of Example 2, the patient reported that her skin had greater elasticity and turgor and that her skin was less wrinkled. The patient also reported that the cream had a pleasant feel.

Case History 2: A seventy three year old female applied the skin cream, prepared according to the method of Example 2, to the skin on her face and on the backs of her hands. After one week, the patient felt that the skin of her hands and face "looked younger".

Case History 3: A forty eight year old female reported vaginal dryness and associated dyspareunia. She had been on oral estrogen replacement therapy since the age of thirty six, after a therapeutic hysterectomy and oophorectomy for severe fibroids. After applying the vaginal ointment prepared according to the method of Example 2 to her vagina once a day for a two week period, the patient experienced a general amelioration of both the dryness and the dyspareunia. In addition, the patient felt that her condition was "at least a little better" even one month after the two week trial period.

Case History 4: A forty year old regularly menstruating female physician with a benign past medical history complained of oily skin. She applied the skin cream prepared according to Alternative Method 1 of Example 3, with 3% pomegranate rind extract, to her skin for a two week period. She reported a very positive effect, encompassing not only a marked reduction of the excess skin oil to about one-half of former levels, but also improved turgor, elasticity and texture. She felt that the improvement ended about one month after the two week trial, but expressed a desire to resume treatment.

While the invention has been described with respect to a limited number of embodiments, it will be appreciated that many variations, modifications and other applications of the invention may be made.

What is claimed is:

1. A method of preparing an oral phytoestrogen supplement comprising the steps of:
   (a) contacting pomegranate seeds with an appropriate solvent to form a pomegranate extract, said solvent being substantially non-toxic for oral administration, said extract being suitable for oral administration;
   (b) contacting an herbal mixture with water to form an aqueous extract, said herbal mixture including schizandra berries and Chinese asparagus root; and
   (c) mixing said aqueous extract with said pomegranate extract to form a mixture, said mixture forming the phytoestrogen supplement.

2. The method of claim 1, further comprising the steps of:
   (d) filtering said mixture from step (c) through a filter to form a filtered mixture and a solid material, said solid material remaining on said filter after the step of filtering said mixture;
   (e) heating said solid material until said solid material is substantially carbonized, forming carbonized solid material;
   (f) extracting said carbonized solid material with water to form a second aqueous extract; and
   (g) mixing said second aqueous extract with said filtered mixture from step (d) to form a second mixture, said second mixture forming the phytoestrogen supplement.

3. The method of claim 1, wherein said herbal mixture further includes Chinese licorice root and Chinese angelica root.

4. The method of claim 3, wherein the ratio of said Chinese licorice root to said Chinese asparagus root to said Chinese angelica root to said schizandra berries is about 2:2:1:2.

5. The method of claim 4, wherein a weight of said Chinese licorice root is about 300 g, a weight of said Chinese asparagus root is about 300 g, a weight of said Chinese angelica root is about 150 g and a weight of said schizandra berries is about 300 g.

6. An oral phytoestrogen supplement, comprising a pomegranate extract, said pomegranate extract being prepared by contacting pomegranate seeds with an appropriate solvent, said solvent being substantially nontoxic for oral administration, and an aqueous extract, said aqueous extract being prepared by contacting an herbal mixture with water, said herbal mixture including schizandra berries and Chinese asparagus root.

7. The phytoestrogen supplement of claim 6, wherein said phytoestrogen supplement further comprises a second aqueous extract, said second aqueous extract being prepared by contacting carbonized solid material with water, said carbonized solid material being prepared by heating solid material until said solid material is substantially carbonized, and said solid material being prepared by filtering said pomegranate extract and said herbal aqueous extract to remove said solid material.

8. A method of preparing an ointment, comprising the following steps:
(a) preparing pomegranate oil by pressing pomegranate seeds; and
(b) mixing said pomegranate oil with coconut milk to form a mixture said mixture forming the ointment.

9. The method of claim 8, further comprising the steps of:
(c) preparing an extract of Chinese asparagus root and schizandra berries by contacting said Chinese asparagus root and said schizandra berries with ethanol; and
(d) adding said extract to said mixture from step (b) to form the ointment.

10. The method of claim 9, further comprising the step of:
(e) adding a pharmaceutically appropriate carrier to said ointment for step (d).

11. The method of claim 10, wherein said pharmaceutically appropriate carrier includes beeswax and cocoa butter.

12. The method of claim 10, wherein said pharmaceutically appropriate carrier includes hydrophilic lanolin.

13. The method of claim 9, wherein a ratio of said pomegranate oil to said coconut milk to said Chinese asparagus root to said schizandra berries is about 40:20:3:3.

14. The method of claim 13, wherein a weight of said pomegranate oil is about 40 g, a weight of said coconut milk is about 20 g, a weight of said Chinese asparagus root is about 3 g and a weight of said schizandra berries is about 3 g.

15. An ointment, comprising an ointment prepared according to the method of claim 8.

16. The ointment of claim 15, wherein said ointment further includes an extract of Chinese asparagus root and schizandra berries, said extract being prepared by contacting said Chinese asparagus root and said schizandra berries with ethanol.

17. The ointment of claim 16, wherein said ointment further includes a pharmaceutically appropriate carrier.

18. The ointment of claim 17, wherein said pharmaceutically appropriate carrier includes beeswax and cocoa butter.

19. The ointment of claim 17, wherein said pharmaceutically appropriate carrier includes hydrophilic lanolin.

20. The ointment of claim 16, wherein a ratio of said pomegranate oil to said coconut milk to said Chinese asparagus root to said schizandra berries is about 40:20:3:3.

21. The ointment of claim 20, wherein a weight of said pomegranate oil is about 40 g, a weight of said coconut milk is about 20 g, a weight of said Chinese asparagus root is about 3 g and a weight of said schizandra berries is about 3 g.

22. A method of preparing an ointment, comprising the steps of:
(a) preparing a ointment according to the method of claim 8, and
(b) adding a pomegranate rind extract to said ointment to form the ointment.

* * * * *